United States Patent
Knight et al.

(10) Patent No.: US 8,182,788 B2
(45) Date of Patent: May 22, 2012

(54) METHOD FOR OBTAINING A 2-$^{18}$F FLUOR-2-DEOXY-D-GLUCOSE $^{18}$F-FDG-SOLUTION

(75) Inventors: Hector Humberto Knight, Alkmaar (NL); Petrus Simon Kruijer, Naarden (NL)

(73) Assignee: Mallinckrodt LLC, Hazelwood, MO (US)

( * ) Notice: Subject to any disclaimer, the term of this patent is extended or adjusted under 35 U.S.C. 154(b) by 1670 days.

(21) Appl. No.: 10/510,454

(22) PCT Filed: Apr. 23, 2003

(86) PCT No.: PCT/US03/12603
§ 371 (c)(1),
(2), (4) Date: Oct. 4, 2004

(87) PCT Pub. No.: WO03/090789
PCT Pub. Date: Nov. 6, 2003

(65) Prior Publication Data
US 2005/0175536 A1     Aug. 11, 2005

(30) Foreign Application Priority Data
Apr. 24, 2002   (EP) .................................. 02076638

(51) Int. Cl.
*A61K 51/00*   (2006.01)
*A61M 36/14*   (2006.01)
*A61K 551/00*   (2006.01)
(52) U.S. Cl. ..................................... 424/1.11; 424/1.89
(58) Field of Classification Search .................. 424/1.89
See application file for complete search history.

(56) References Cited

U.S. PATENT DOCUMENTS

| 4,707,353 | A |   | 11/1987 | Bugaj et al. |
| 5,308,944 | A | * | 5/1994 | Stone-Elander et al. ..... 219/687 |
| 5,536,491 | A | * | 7/1996 | Asai et al. ................. 424/9.363 |
| 6,172,207 | B1 | * | 1/2001 | Damhaut et al. ............. 536/18.4 |

FOREIGN PATENT DOCUMENTS

| WO | WO 92/00758 |      | 1/1992 |
| WO | WO 9815295  | A2   | 4/1998 |

OTHER PUBLICATIONS

Manual for PET-Radiopharmaceutical Dispensing Unit (Revision dated Oct. 12, 2001); Nuclear Interface GmbH.
FDG Synthesizers, Supplement to the Manual and Operating Instructions (Revision dated Nov. 21, 2001); Nuclear Interface GmbH.
"Sterilization of FDG"; Selected Information about the Dispenser/Sterilizer. GE Medical Systems Functional Imaging GmbH, Dorotheenstr. 26a, D-48145 Münster.
Irie T. et.al. "Aspects of the preparation of 18F-2-deoxy-2-fluoro-D-glucose (18FDG) for medical use." Radioisotopes Japan. Jan. 1982, vol. 31, No. 1, Jan. 1982 pp. 11-15. XP008009483.

* cited by examiner

*Primary Examiner* — Michael G Hartley
*Assistant Examiner* — Melissa Perreira

(57) ABSTRACT

The invention relates to a method for improving one or more physical/chemical characteristics, like reduced radiolysis of and the ability to autoclave, a 18F-fluor-deoxy-glucose (18F-FDG)-solution, which method comprises the steps of a) provision of a 18F-fluor-deoxy-glucose (18F-FDG)-solution, and b) addition of at least one buffer based on a weak acid to the 18F-fluor-deoxy-glucose (18F-FDG)-solution. The invention also relates to a method for preparing a sterile 18F-fluor-deoxy-glucose (18F-FDG)-solution by autoclaving said 18F-fluor-deoxy-glucose (FDG)-solution.

14 Claims, No Drawings

METHOD FOR OBTAINING A 2-$^{18}$F FLUOR-2-DEOXY-D-GLUCOSE $^{18}$F-FDG-SOLUTION

The present invention relates to a method for obtaining a 2-[$^{18}$F]fluor-2-deoxy-D-glucose (also described herein as $^{18}$F-fluor-deoxy-glucose or $^{18}$F-FDG)-solution with improved physical/chemical characteristics, i.e. radiochemical stability, and a (sterile) $^{18}$F-FDG-solution thus obtained.

In recent years, in the field of Nuclear Medicine, the compound $^{18}$F-FDG, aside from important uses in cardiology and neurology, has shown an ability to detect cancerous tissues undetectable by conventional means or to correct misdiagnosis of the disease. This is due to exploiting a fundamental change that occurs in cells when they become malignant; cancer cells lose their ability to efficiently convert glucose into energy. Consequently, they require much more glucose, up to 20 to 50 times more.

$^{18}$F-FDG is usually prepared with the help of a fully automated synthesizer. Because the compound needs to be injected in patients, it is required that the solution containing the compound is sterilized prior to injection. However, the radiochemical purity of the compound decreases drastically during standard autoclaving steps and thus the compound fails to meet the specifications dictated by the European and United States Pharmacopeia. In addition, after synthesis, $^{18}$F-FDG rapidly loses in radiochemical purity due to both radiolysis and the half-life of the radioisotope, limiting the period in which the compound can be used.

It is the object of the present invention to provide a $^{18}$F-fluor-deoxy-glucose (FDG)-solution which can be autoclaved while still meeting the specification of more than 95% radiochemical purity eight hours after production. In addition, it is the object of the present invention to reduce, after synthesis, the effect of radiolysis of $^{18}$F-FDG in solution.

In the research leading to the present invention, it has been found that buffering the $^{18}$F-FDG-solution has a strong effect on the physical/chemical characteristics, i.e. the radiostability. It has been surprisingly found that buffers based on a weak acid improve the physical/chemical characteristics, i.e. the radiostability, of a $^{18}$F-FDG-solution to such extent that it becomes possible to autoclave this solution and maintain a radiochemical purity of at least 95%.

This is achieved according to the invention by a method comprising the following steps:
  a) provision of a $^{18}$F-fluor-deoxy-glucose ($^{18}$F-FDG)-solution, and
  b) addition of at least one buffer based on a weak acid to the $^{18}$F-FDG-solution.

The weak acid buffer should be physiologically acceptable and is preferably a citrate buffer, an acetate buffer, an ascorbate buffer or a combination of these buffers.

The improved physical/chemical characteristics of the $^{18}$F-FDG-solution are obtained when the pH of the citrate buffer is lower than 5.5, in particular between 2 and 5.5. For the acetate buffer, these characteristics are obtained at pH values between 3.0 and 5.5. The ascorbate buffer is used in a similar pH range as the acetate buffer between 3.0 and 5.5.

Autoclaving of the 18F-FDG-solution is performed at a temperature between 110° C. and 150° C., preferably at a temperature between 130° C. and 140° C. and more preferably at a temperature of 134° C. It was found that these temperatures are optimal considering stability and half-life of the 18F radio-isotope. The autoclaving process of the 18F-FDG-solution is performed during 1 to 30 minutes, preferably during 1 to 10 minutes and more preferably during 2 to 5 minutes. These ranges have been optimized considering the relatively short half-life of the 18F radio-isotope, which is 109.8 minutes.

The present invention will be further elucidated in the examples that follow and which are given for illustration purposes only and are not limiting the scope of the invention.

EXAMPLES

Example 1

Autoclaving of a $^{18}$F-FDG-Solution at pH Range 4.5 to 5.5

In this example, three test runs have been performed to study the radiochemical purity of a $^{18}$F-fluor-deoxy-glucose (FDG)-solution buffered with a weak acid as compared to the non-buffered solution in saline.

Directly after production, the $^{18}$F-fluor-deoxy-glucose (FDG)-solution is diluted with saline to a radioactive concentration of 3 mCi/ml at ART (Activity Reference Time) (t=0). Two hours after production, vials with 0.5 ml of $^{18}$F-fluor-deoxy-glucose (FDG)-solution were prepared, mixed with 0.1 ml of buffer (10 mM) and then autoclaved.

Table 1 illustrates the radiochemical purity of the differently buffered $^{18}$F-fluor-deoxy-glucose (FDG)-solutions after autoclaving during 5 minutes at 134° C. Measurements were carried out directly after autoclaving using a KAVO Sterimaster™.

TABLE 1

Autoclaving of the $^{18}$F-FDG-solution at pH ranges 4.5 to 5.5

| | Radiochemical purity of $^{18}$F-FDG (%) | | |
|---|---|---|---|
| | Test 1 | Test 2 | Test 3 |
| Not autoclaved | 98.85 | 96.41 | 95.9 |
| Autoclaved Buffer/pH | | | |
| Ascorbate/4.5 | 94.5 | 95.0 | 94.7 |
| Ascorbate/5.5 | 94.1 | 94.4 | 94.5 |
| Citrate/4.5 | 97.3 | 96.5 | 96.3 |
| Citrate/5.5 | 94.5 | 95.3 | 94.1 |
| Acetate/4.5 | 96.5 | 94.6 | 94.5 |
| Acetate/5.5 | 94.5 | 92.5 | 92.5 |
| NaCl/6.2 (reference) | 92.4 | 90.9 | 91.1 |

All the buffers tested gave a higher radiochemical purity than the non-buffered reference sample NaCl/pH 6.2. The buffer giving the best results is the citrate buffer with a pH of 4.5. As compared to the not autoclaved samples, only one out of three experiments showed a decrease in the radiochemical purity of 1% (test 1).

Example 2

Autoclaving $^{18}$F-FDG-Solution at Low pH-Ranges (pH 2-3)

In this example, two test runs have been performed to study the radiochemical purity of a $^{18}$F-fluor-deoxy-glucose (FDG)-solution buffered with a weak acid to pH 2-3.

Directly after production, the $^{18}$F-fluor-deoxy-glucose (FDG)-solution is diluted with saline to a radioactive concentration of 3 mCi/ml at ART (12:00 h). Two 10 hours after production, vials with 0.5 ml of $^{18}$F-fluor-deoxy-glucose (FDG)-solution were prepared, mixed with 0.1 ml of buffer (100 mM) and then autoclaved.

Table 2 illustrates the radiochemical purity of the differently buffered $^{18}$F-fluor-deoxy-glucose (FDG)-solutions after autoclaving during 5 minutes at 134° C.

TABLE 2

Autoclaving $^{18}$F-FDG-solution at low pH-ranges (pH 2-3)

| Buffer | pH | Radiochemical purity of $^{18}$F-FDG (%) | |
|---|---|---|---|
| | | test 1 | test 2 |
| Ascorbate | 3.0 | 97.8 | 98.0 |
| Citrate | 2.0 | 98.7 | 98.5 |
| Acetate | 3.0 | 97.4 | 97.3 |
| NaCl (reference) | 6.2 | 90.9 | 91.1 |

All three buffers tested yielded a higher radiochemical purity than the non-buffered reference sample NaCl/pH 6.2. Compared to the reference sample (decrease in radiochemical purity 9%) only a 2-3% decrease in radiochemical purity was observed for the samples buffered with a weak acid. For all buffers (ascorbate, citrate and acetate), no significant decrease in the radiochemical purity was measured as compared to the non-autoclaved samples (Table 1).

Example 3

Radiolysis of $^{18}$F-FDG

The radiolysis of $^{18}$F-FDG was measured during a period of approximately 8.5 hours. The radioactive concentration was 3 mCi/ml at ART (t=0).

Two buffers were tested and compared to the reference sample in 0.9$ NaCl/pH 6.9. The first buffer was a citrate buffer pH 4.5 and the second buffer an ascorbate buffer pH 4.5. Five determinations of the radiochemical purity of the samples were conducted during the interval. The results are illustrated in table 3.

TABLE 3

Radiolysis of a $^{18}$F-fluor-deoxy-glucose (FDG)-solution.

| buffer/pH | time of determination (min) | percentage $^{18}$F-FDG |
|---|---|---|
| citrate buffer, pH 4.5 | 0 | 98.98 |
| | 46 | 98.03 |
| | 203 | 96.18 |
| | 317 | 95.31 |
| | 495 | 94.73 |
| ascorbate buffer, pH 4.5 | 0 | 98.98 |
| | 64 | 97.96 |
| | 213 | 97.55 |
| | 327 | 97.37 |
| | 505 | 97.28 |
| 0.9% NaCl, pH 6.90 | 0 | 98.98 |
| | 94 | 96.51 |
| | 230 | 94.74 |
| | 340 | 94.13 |
| | 516 | 93.59 |

Radiolysis in both buffers tested was decreased as compared to the 0.9% NaCl sample. The largest decrease in radiolysis was observed when using the ascorbate buffer. Only a 2% decrease in activity was observed after 8.5 hours. This decrease was 4% and 6% for the citrate buffer and the 0.9% NaCl, respectively. In conclusion, $^{18}$F-FDG is more stable after addition of an ascorbate or citrate buffer than without the addition of these buffers.

Example 4

Autoclaving and Radiolysis of $^{18}$F-fluor-deoxy-glucose (FDG)-Solutions

The radiolysis of $^{18}$F-FDG was measured during a period of approximately 7.5 hours after autoclaving the sample. Two buffers were tested and compared to the reference sample in 0.9% NaCl/pH 6.9. The first was a citrate buffer pH 4.5 and the second an ascorbate buffer pH 4.5. Three determinations of the radiochemical purity of the samples were conducted during the interval. The results are illustrated in table 4.

TABLE 4

Autoclaving and radiolysis of a $^{18}$F-fluor-deoxy-glucose (FDG)-solution

| Time of determination (min) | Radiochemical purity of $^{18}$F-FDG (%) | | | |
|---|---|---|---|---|
| | autoclaved | | | not autoclaved |
| | citrate | ascorbate | NaCl | NaCl |
| 0 | 97.37 | 95.56 | 89.56 | 97.49 |
| 240 | 95.55 | 94.65 | 87.49 | 95.30 |
| 453 | 95.35 | 94.50 | 86.77 | 94.61 |

After addition of a weak acid buffer $^{18}$F-FDG is stable under autoclavation conditions. Without addition of this buffer, the radiochemical purity of the sample drops dramatically to less than 90%. A citrate buffer yields better stability of the $^{18}$F-FDG-solution as compared to ascorbate. In addition, radiolysis, after autoclaving, in both buffers tested was decreased as compared to the NaCl sample. The largest decrease in radiolysis was observed when the ascorbate buffer was used. Only a 1% decrease in activity was observed after 7.5 hours. This decrease was 2% and 3% for the citrate buffer and the NaCl sample, respectively. In conclusion, the $^{18}$F-FDG-solution is more stable after addition of an ascorbate or citrate buffer than without the presence of these buffers during autoclavation. After autoclaving, in both buffers the radiolysis of the $^{18}$F-FDG-solution was reduced.

The invention claimed is:

1. A method for improving radiostability of a $^{18}$F-fluor-deoxy-glucose ($^{18}$F-FDG)-solution during autoclaving, the method comprising:
    a) providing a $^{18}$F-fluor-deoxy-glucose ($^{18}$F-FDG)-solution,
    b) adding at least one buffer based on a weak acid to the $^{18}$F-fluor-deoxy-glucose ($^{18}$F-FDG)-solution, wherein the buffer is selected from the group consisting of citrate, acetate, ascorbate and combinations thereof; and,
    c) autoclaving the buffered $^{18}$F-fluor-deoxy-glucose ($^{18}$F-FDG)-solution.

2. The method according to claim 1, wherein the buffered $^{18}$F-FDG-solution maintains radiochemical purity after being autoclaved, thus rendering the solution suitable for medical applications.

3. The method according to claim 1, wherein the pH of the citrate buffer is lower than 5.5.

4. The method according to claim 1, wherein the pH of the acetate buffer is between 3.0 and 5.5.

5. The method according to claim 1, wherein the pH of the ascorbate buffer is between 3.0 and 5.5.

6. The method according to claim 1, wherein the buffered $^{18}$F-fluor-deoxy-glucose (FDG)-solution is autoclaved at a temperature between 110° C. and 145° C.

7. The method according to claim 1, wherein the buffered $^{18}$F-fluor-deoxy-glucose (FDG)-solution is autoclaved at a temperature between 130° C. and 140° C.

8. The method according to claim 1, wherein the buffered $^{18}$F-fluor-deoxy-glucose (FDG)-solution is autoclaved at a temperature of 134° C.

9. The method according to claim 6, wherein autoclaving is performed for a period of 1 to 30 minutes.

10. The method according to claim 6, wherein autoclaving is performed for a period of 1 to 10 minutes.

11. The method according to claim 6, wherein autoclaving is performed for a period of 2 to 5 minutes.

12. The method of claim 2, wherein the radiochemical purity of the buffered $^{18}$F-fluor-deoxy-glucose ($^{18}$F-FDG)-solution is at least 95%.

13. The method accordingly to claim 12, wherein the radiochemical purity of the buffered $^{18}$F-FDG-solution is at least about 95% 7.5 hours after being autoclaved.

14. The method according to claim 3, wherein the pH of the citrate buffer is between 2 and 5.5.

* * * * *